(12) United States Patent
Wilson

(10) Patent No.: US 6,254,593 B1
(45) Date of Patent: *Jul. 3, 2001

(54) BIFURCATED STENT DELIVERY SYSTEM HAVING RETRACTABLE SHEATH

(75) Inventor: W. Stan Wilson, Missoula, MT (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/459,004

(22) Filed: Dec. 10, 1999

(51) Int. Cl.$^7$ ........................................... A61F 2/06

(52) U.S. Cl. ............................................ 606/1.11; 623/1.35

(58) Field of Search .................................. 606/194, 192, 606/195, 198; 604/96.1, 101.01, 101.02, 101.03; 623/1.11, 1.36, 1.35

(56) References Cited

U.S. PATENT DOCUMENTS

| D. 376,011 | 11/1996 | Nunokawa . |
|---|---|---|
| 2,845,959 | 8/1958 | Sidebotham . |
| 2,978,787 | 4/1961 | Liebig . |
| 2,990,605 | 7/1961 | Demsyk . |

(List continued on next page.)

FOREIGN PATENT DOCUMENTS

| 0 461 791 A1 | 12/1991 | (EP) . |
|---|---|---|
| 0 466 518 A3 | 1/1992 | (EP) . |
| 0 747 020 A2 | 2/1996 | (EP) . |
| 0 804 907 | 11/1997 | (EP) . |
| 2 737 969 | 2/1997 | (FR) . |
| 1217402 | 3/1986 | (RU) . |
| 1318235 A1 | 6/1987 | (RU) . |
| 1389778 A2 | 4/1988 | (RU) . |
| 1457921 A1 | 2/1989 | (RU) . |
| 1482714 A2 | 5/1989 | (RU) . |
| WO 95/16406 | 6/1995 | (WO) . |
| WO 95/21592 | 8/1995 | (WO) . |

(List continued on next page.)

OTHER PUBLICATIONS

Lawrence, David D., Jr., M.D., et al., Percutaneous Endovascular Graft: Experimental Evaluation, *Radiology*, vol. 163, No. 2, pp. 357–360 (1987).

Yoshioka, Tetsuya, et a., Self–Expanding Endovascular Graft: An Experimental Study in Dogs, *Radiology*, vol. 170, pp. 1033–1037 (1989).

Parodi, J.C., M.D., et al., Transfemoral Intraluminal Graft Implantation for Abdominal Aortic Aneuyrsms, *Annals of Vascular Surgery*, vol. 5, No. 6, pp. 491–499 (1991).

Mirich, David, M.D., Percutaneously Placed Endovascular Grafts for Aortic Aneurysms: Feasibility Study,*Radiology*, vol. 170, No. 3, Part 2, pp. 1033–1037 (1989).

Chuter, Timothy A.M., BM, BS, et al., Transfemoral Endovascular Aortic Graft Placement, *Journal of Vascular Surgery*, pp. 185–196 (Aug. 1993).

Bard XT Catina Bifurcate Stent (Brochure) (Undated).

*Primary Examiner*—Henry J. Recla
*Assistant Examiner*—Kevin Truong
(74) *Attorney, Agent, or Firm*—Fulwider Patton Lee & Utecht, LLP

(57) ABSTRACT

An improved catheter assembly and method are provided for treating bifurcated vessels. The catheter assembly of the present invention includes a tubular sheath for restraining dual balloons normally biased apart. Withdrawal of the sheath allows the balloons to separate and deploy intravascular stents in a bifurcated vessel. The catheter assembly also includes the feature of containing two guide wire lumens in a single catheter designed to track over a single wire prior to arrival at the bifurcation, thus preventing wire wrapping and crossing of the wires.

7 Claims, 9 Drawing Sheets

U.S. PATENT DOCUMENTS

| | | |
|---|---|---|
| 3,029,819 | 4/1962 | Starks . |
| 3,096,560 | 7/1963 | Liebig . |
| 3,142,067 | 7/1964 | Liebig . |
| 3,657,744 | 4/1972 | Ersek . |
| 3,908,662 | 9/1975 | Razgulov et al. . |
| 3,945,052 | 3/1976 | Liebig . |
| 4,041,931 | 8/1977 | Elliott et al. . |
| 4,047,252 | 9/1977 | Liebig et al. . |
| 4,061,134 | 12/1977 | Samuels et al. . |
| 4,108,161 | 8/1978 | Samuels et al. . |
| 4,140,126 | 2/1979 | Choudhury . |
| 4,193,137 | 3/1980 | Heck . |
| 4,202,349 | 5/1980 | Jones . |
| 4,214,587 | 7/1980 | Sakura, Jr. . |
| 4,517,687 | 5/1985 | Liebirg et al. . |
| 4,560,374 | 12/1985 | Hammerslag . |
| 4,562,596 | 1/1986 | Kornberg . |
| 4,577,631 | 3/1986 | Kreamer . |
| 4,617,932 | 10/1986 | Kornberg . |
| 4,652,263 | 3/1987 | Herweck et al. . |
| 4,693,249 | 9/1987 | Schenck et al. . |
| 4,728,328 | 3/1988 | Hughes et al. . |
| 4,732,152 | 3/1988 | Wallsten et al. . |
| 4,739,762 | 4/1988 | Palmaz . |
| 4,787,899 | 11/1988 | Lazarus . |
| 4,793,348 | 12/1988 | Palmaz . |
| 4,795,458 | 1/1989 | Regan . |
| 4,795,465 | 1/1989 | Marten . |
| 4,830,003 | 5/1989 | Wolff et al. . |
| 4,872,874 | 10/1989 | Taheri . |
| 4,878,906 | 11/1989 | Lindemann et al. . |
| 4,892,539 | 1/1990 | Koch . |
| 4,969,890 | 11/1990 | Sugita et al. . |
| 4,969,896 | 11/1990 | Shors . |
| 4,994,071 | 2/1991 | MacGregor . |
| 5,026,377 | 6/1991 | Burton et al. . |
| 5,047,050 | 9/1991 | Arpesani . |
| 5,104,339 | 4/1992 | Lazarus . |
| 5,108,424 | 4/1992 | Hoffman, Jr. et al. . |
| 5,127,919 | 7/1992 | Ibrahim et al. . |
| 5,156,619 | 10/1992 | Ehrenfeld . |
| 5,178,630 | 1/1993 | Schmitt . |
| 5,178,634 | 1/1993 | Ramos-Martinez . |
| 5,197,976 | 3/1993 | Herweck et al. . |
| 5,197,977 | 3/1993 | Hoffman, Jr. et al. . |
| 5,304,220 | 4/1994 | Maginot . |
| 5,316,023 | 5/1994 | Palmaz et al. . |
| 5,360,443 | 11/1994 | Barone et al. . |
| 5,443,497 | 8/1995 | Venbrux . |
| 5,443,498 | 8/1995 | Fontaine . |
| 5,456,712 | 10/1995 | Maginot . |
| 5,522,880 | 6/1996 | Barone et al. . |
| 5,527,355 | 6/1996 | Ahn . |
| 5,562,724 | 10/1996 | Chuter . |
| 5,571,170 | 11/1996 | Palmaz et al. . |
| 5,571,171 | 11/1996 | Barone et al. . |
| 5,571,173 | 11/1996 | Parodi . |
| 5,575,817 | 11/1996 | Martin . |
| 5,578,072 | 11/1996 | Parodi . |
| 5,591,228 | 1/1997 | Edoga . |
| 5,591,229 | 1/1997 | Parodi . |
| 5,603,721 | 2/1997 | Lau et al. . |
| 5,609,627 | 3/1997 | Goiocoechea et al. . |
| 5,613,980 | 3/1997 | Chauhan . |
| 5,617,878 | 4/1997 | Taheri . |
| 5,632,763 | 5/1997 | Glastra . |
| 5,639,278 | 6/1997 | Dereume et al. . |
| 5,643,340 | 7/1997 | Nunokawa . |
| 5,669,924 | 9/1997 | Shaknovich . |
| 5,676,696 | 10/1997 | Marcade . |
| 5,676,697 | 10/1997 | McDonald . |
| 5,683,450 | 11/1997 | Goicoechea et al. . |
| 5,683,452 | 11/1997 | Barone et al. . |
| 5,683,453 | 11/1997 | Palmaz . |
| 5,693,084 | 12/1997 | Chuter . |
| 5,693,086 | 12/1997 | Goicoechea et al. . |
| 5,693,087 | 12/1997 | Parodi . |
| 5,693,088 | 12/1997 | Lazarus . |
| 5,695,517 | 12/1997 | Marin et al. . |
| 5,709,713 | 1/1998 | Evans et al. . |
| 5,713,917 | 2/1998 | Leonhardt et al. . |
| 5,718,724 | 2/1998 | Goicoechea et al. . |
| 5,720,735 | 2/1998 | Dorros . |
| 5,749,825 | 5/1998 | Fischell et al. . |
| 5,755,734 | 5/1998 | Richter et al. . |
| 5,755,735 * | 5/1998 | Richter et al. ..................... 606/194 |
| 5,755,771 * | 5/1998 | Penn et al. ........................... 606/194 |
| 5,776,180 | 7/1998 | Goicoechea et al. . |
| 5,782,906 | 7/1998 | Marshall et al. . |
| 5,800,508 | 9/1998 | Goicoechea et al. . |
| 5,800,520 | 9/1998 | Fogarty et al. . |
| 5,827,320 | 10/1998 | Richter et al. . |
| 5,893,887 | 4/1999 | Jayaraman . |
| 5,895,407 | 4/1999 | Jayaraman . |
| 5,916,234 | 6/1999 | Lam . |
| 5,916,263 | 6/1999 | Goicoechea et al. . |
| 5,919,225 | 7/1999 | Lau et al. . |
| 5,921,995 | 7/1999 | Kleshinski . |
| 5,938,696 | 8/1999 | Goicoechea et al. . |
| 5,954,693 | 9/1999 | Barry . |
| 5,972,017 | 10/1999 | Berg . |
| 5,976,155 | 11/1999 | Foreman et al. . |
| 6,030,413 | 2/2000 | Lazarus . |
| 6,030,414 | 2/2000 | Taheri . |
| 6,030,415 | 2/2000 | Chuter . |
| 6,033,434 | 3/2000 | Borghi . |
| 6,033,435 | 3/2000 | Penn et al. . |
| 6,039,754 | 3/2000 | Caro . |
| 6,048,361 | 4/2000 | Von Oepen . |
| 6,051,020 | 4/2000 | Goicoechea et al. . |
| 6,096,073 | 8/2000 | Webster et al. . |

FOREIGN PATENT DOCUMENTS

| | | |
|---|---|---|
| WO 96/23455 | 8/1996 | (WO) . |
| WO 96/24306 | 8/1996 | (WO) . |
| WO 96/24308 | 8/1996 | (WO) . |
| WO 96/34580 | 11/1996 | (WO) . |
| WO 97/07752 | 3/1997 | (WO) . |
| WO 97/ | 5/1997 | (WO) . |
| WO 97/15345 | 5/1997 | (WO) . |
| WO 98/19628 | 10/1997 | (WO) . |
| WO 97/41803 | 11/1997 | (WO) . |
| WO 97/45073 | 12/1997 | (WO) . |
| WO 98/36709 | 2/1998 | (WO) . |

* cited by examiner

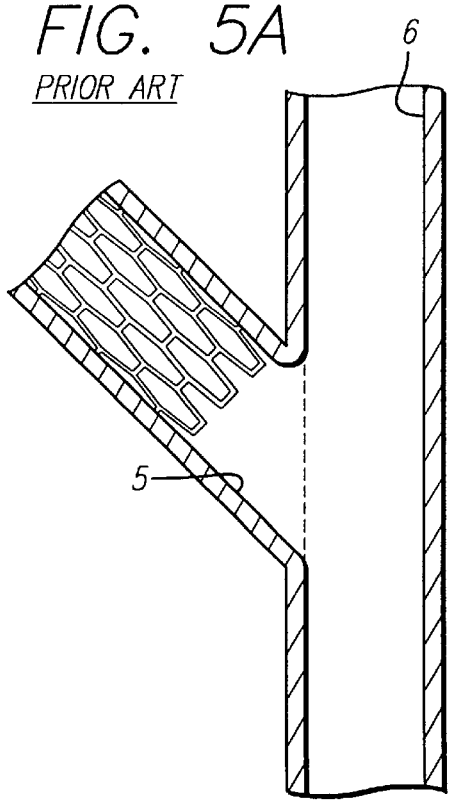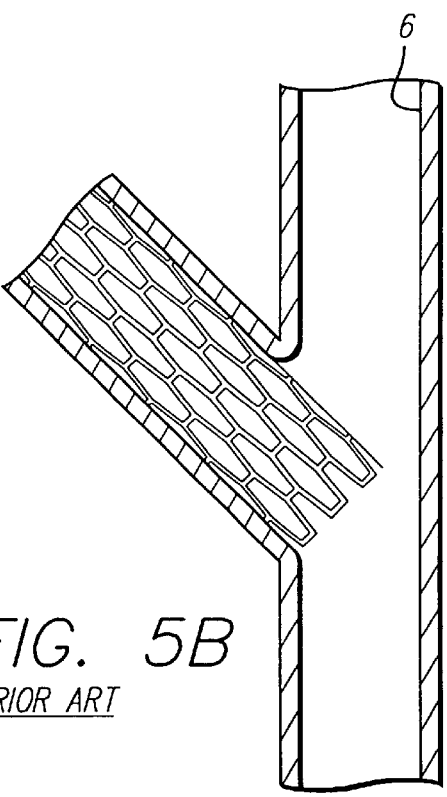
FIG. 5A PRIOR ART
FIG. 5B PRIOR ART

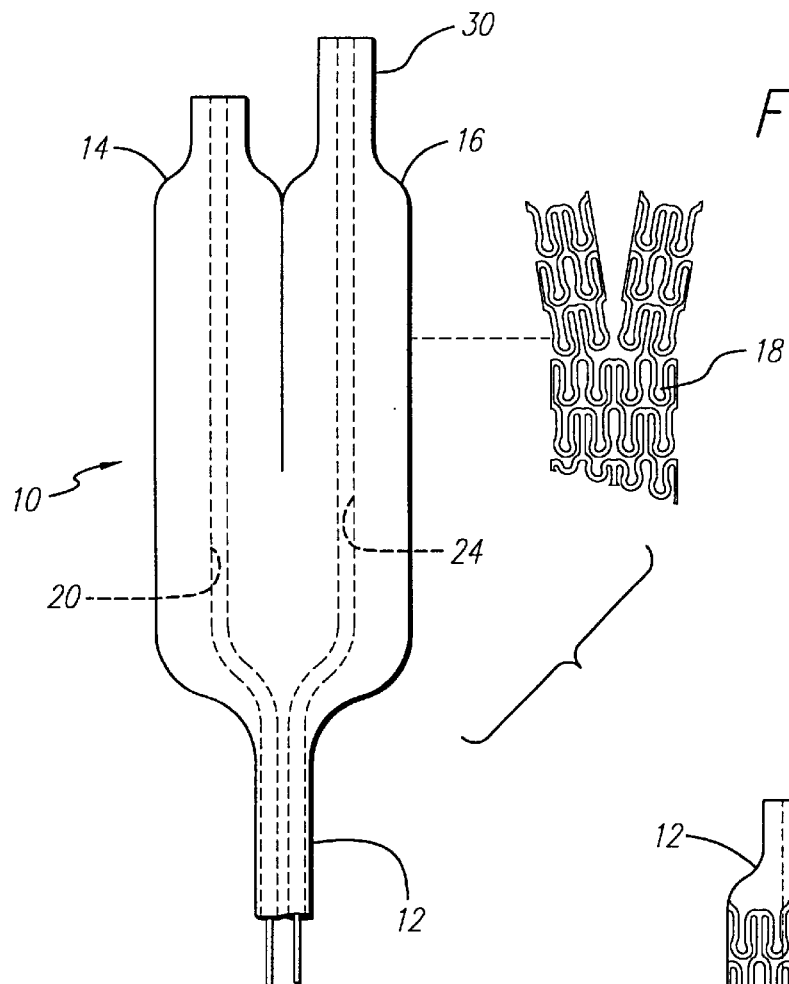
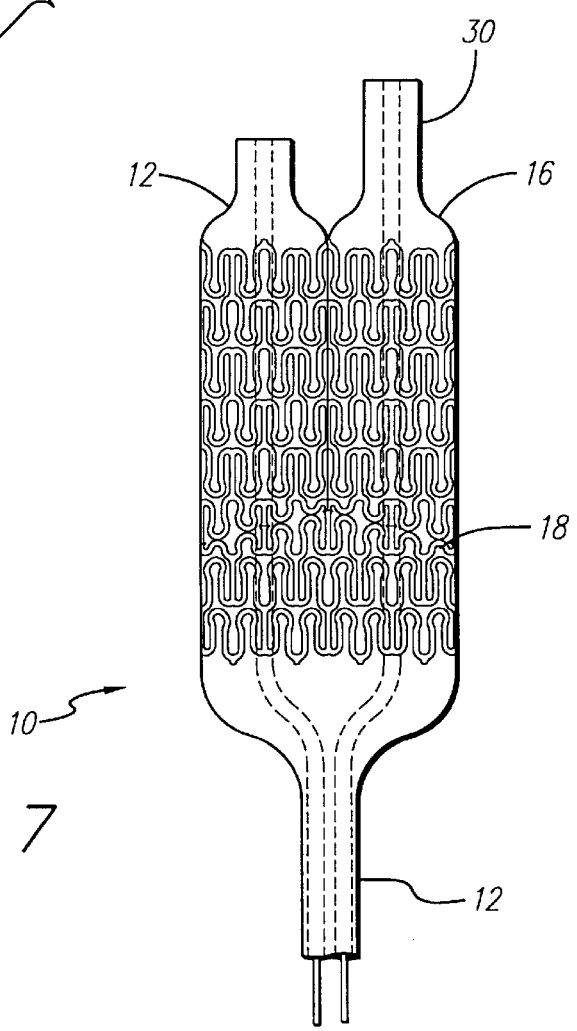
FIG. 6
FIG. 7

BIFURCATED STENT DELIVERY SYSTEM HAVING RETRACTABLE SHEATH

BACKGROUND OF THE INVENTION

The invention relates to a stent delivery system for use at a bifurcation and, more particularly, a bifurcated stent delivery system having a retractable sheath.

Stents conventionally repair blood vessels that are diseased. Stents are generally hollow and cylindrical in shape and have terminal ends that are generally perpendicular to their longitudinal axes. In use, the conventional stent is positioned at the diseased area of a vessel and, after placement, the stent provides an unobstructed pathway for blood flow.

Repair of vessels that are diseased at a bifurcation is particularly challenging since the stent must overlay the entire diseased area at the bifurcation, yet not itself compromise blood flow. Therefore, the stent must, without compromising blood flow, overlay the entire circumference of the ostium to a diseased portion and extend to a point within and beyond the diseased portion. Where the stent does not overlay the entire circumference of the ostium to the diseased portion, the stent fails to completely repair the bifurcated vessel. Where the stent overlays the entire circumference of the ostium to the diseased portion, yet extends into the junction comprising the bifurcation, the diseased area is repaired, but blood flow may be compromised in other portions of the bifurcation. Unopposed stent elements may promote lumen compromise during neointimalization and healing, producing restenosis and requiring further procedures. Moreover, by extending into the junction comprising the bifurcation, the stent may block access to portions of the bifurcated vessel that require performance of further interventional procedures. Similar problems are encountered when vessels are diseased at their angled origin from the aorta as in the ostium of a right coronary or a vein graft. In this circumstance, a stent overlaying the entire circumference of the ostium extends back into the aorta, creating problems, including those for repeat catheter access to the vessel involved in further interventional procedures.

Conventional stents are designed to repair areas of blood vessels that are removed from bifurcations and, since a conventional stent generally terminates at right angles to its longitudinal axis, the use of conventional stents in the region of a vessel bifurcation may result in blocking blood flow of a side branch or fail to repair the bifurcation to the fullest extent necessary. The conventional stent might be placed so that a portion of the stent extends into the pathway of blood flow to a side branch of the bifurcation or extend so far as to completely cover the path of blood flow in a side branch. The conventional stent might alternatively be placed proximal to, but not entirely overlaying, the circumference of the ostium to the diseased portion. Such a position of the conventional stent results in a bifurcation that is not completely repaired. The only conceivable situation in which the conventional stent, having right-angled terminal ends, could be placed where the entire circumference of the ostium is repaired without compromising blood flow, is where the bifurcation is formed of right angles. In such scenarios, extremely precise positioning of the conventional stent is required. This extremely precise positioning of the conventional stent may result with the right-angled terminal ends of the conventional stent overlaying the entire circumference of the ostium to the diseased portion without extending into a side branch, thereby completely repairing the right-angled bifurcation.

To circumvent or overcome the problems and limitations associated with conventional stents in the context of repairing diseased bifurcated vessels, a stent that consistently overlays the entire circumference of the ostium to a diseased portion, yet does not extend into the junction comprising the bifurcation, may be employed. Such a stent would have the advantage of completely repairing the vessel at the bifurcation without obstructing blood flow in other portions of the bifurcation. In addition, such a stent would allow access to all portions of the bifurcated vessel should further interventional treatment be necessary. In a situation involving disease in the origin of an angulated aorto-ostial vessel, such a stent would have the advantage of completely repairing the vessel origin without protruding into the aorta or complicating repeat access.

In addition to the problems encountered by using the prior art stents to treat bifurcations, the delivery platform for implanting such stents has presented numerous problems. For example, a conventional stent is implanted in the main vessel so that a portion of the stent is across the side branch, so that stenting of the side branch must occur through the main-vessel stent struts. In this method, commonly referred to in the art as the "monoclonal antibody" approach, the main-vessel stent struts must be spread apart to form an opening to the side branch vessel and then a catheter with a stent is delivered through the opening. The cell to be spread apart must be randomly and blindly selected by recrossing the deployed stent with a wire. The drawback with this approach is there is no way to determine or guarantee that the main-vessel stent struts are properly oriented with respect to the side branch or that the appropriate cell has been selected by the wire for dilatation. The aperture created often does not provide a clear opening and creates a major distortion in the surrounding stent struts. There is no way to tell if the main-vessel stent struts have been properly oriented and spread apart to provide a clear opening for stenting the side branch vessel.

In another prior art method for treating bifurcated vessels, commonly referred to as the "Culotte technique," the side branch vessel is first stented so that the stent protrudes into the main vessel. A dilatation is then performed in the main vessel to open and stretch the stent struts extending across the lumen from the side branch vessel. Thereafter, the main-vessel stent is implanted so that its proximal end overlaps with the side branch vessel. One of the drawbacks of this approach is that the orientation of the stent elements protruding from the side branch vessel into the main vessel is completely random. Furthermore, the deployed stent must be recrossed with a wire blindly and arbitrarily selecting a particular stent cell. When dilating the main vessel stretching the stent struts is therefore random, leaving the possibility of restricted access, incomplete lumen dilatation, and major stent distortion.

In another prior art device and method of implanting stents, a "T" stent procedure includes implanting a stent in the side branch ostium of the bifurcation followed by stenting the main vessel across the side branch ostium. In another prior art procedure, known as "kissing" stents, a stent is implanted in the main vessel with a side branch stent partially extending into the main vessel creating a double-barreled lumen of the two stents in the main vessel proximal to the bifurcation. Another prior art approach includes a so-called "trouser legs and seat" approach, which includes implanting three stents, one stent in the side branch vessel, a second stent in a distal portion of the main vessel, and a third stent, or a proximal stent, in the main vessel just proximal to the bifurcation.

All of the foregoing stent deployment assemblies suffer from the same problems and limitations. Typically, there are uncovered intimal surface segments on the main vessel and side branch vessels between the stented segments. An uncovered flap or fold in the intima or plaque will invite a "snowplow" effect, representing a substantial risk for subacute thrombosis, and the increased risk of the development of restenosis. Further, where portions of the stent are left unopposed within the lumen, the risk for subacute thrombosis or the development of restenosis again is increased. The prior art stents and delivery assemblies for treating bifurcations are difficult to use, making successful placement nearly impossible. Further, even where placement has been successful, the side branch vessel can be "jailed" or covered so that there is impaired access to the stented area for subsequent intervention.

Attempts to bring any device, such as a bifurcated stent on a bifurcated balloon assembly, to a bifurcation over two wires are prone to the problem of wire wrapping. This phenomenon involves one wire crossing the other first anteriorly then posteriorly. The resulting wrapping then creates resistance to advancement of the device, thus resulting in failure of deployment. Therefore, when delivering a device ultimately utilizing two wires, it would be desirable to first track the device in over a single wire, thus avoiding wire wrapping. The present invention offers a solution to these problems and others.

As used herein, the terms "proximal," "proximally," and "proximal direction" when used with respect to the invention are intended to mean moving away from or out of the patient, and the terms "distal," "distally," and "distal direction" when used with respect to the invention are intended to mean moving toward or into the patient. These definitions will apply with reference to apparatus, such as catheters, guide wires, stents, the like. When used with reference to body lumens, such as blood vessels and the like, the terms "proximal," "proximally," and "proximal direction" are intended to mean toward the heart; and the terms "distal," "distally," and "distal direction" are intended to mean away from the heart, and particularly with respect to a bifurcated blood vessel, are intended to mean in the direction in which the branching occurs.

SUMMARY OF THE INVENTION

The invention provides for a bifurcated stent delivery system having a retractable sheath. The system is designed for repairing a main vessel and a side branch vessel forming a bifurcation, without compromising blood flow in other portions of the bifurcation, thereby allowing access to all portions of the bifurcated vessel should further interventional treatment be necessary. The catheter and the retractable sheath are designed to reduce the likelihood of wire wrapping during the stenting procedure.

In one aspect of the invention, there is provided a stent delivery assembly for treating bifurcated vessels including a dual balloon Y-shaped catheter. The catheter includes a first expandable member and a second expandable member. A first guide wire lumen is provided for receiving a first guide wire. The first guide wire lumen extends through at least a portion of the catheter including the first expandable member. A second guide wire lumen is provided for receiving a second guide wire, the second guide wire lumen extends through at least a portion of the catheter including the second expandable member. A tubular member is provided, wherein the first expandable member and the second expandable member are normally biased apart, but are restrained and held together by the tubular member to provide a low profile during delivery of a Y-shaped stent.

In another aspect of the invention, a method is provided of stenting a bifurcated vessel having a bifurcation, a first vessel branch, and a second vessel branch. The method includes the step of providing a dual balloon Y-shaped catheter having a first expandable member and a second expandable member. A Y-shaped stent is mounted on the first and second expandable members. A tubular member is placed about the first and second expandable members such that the first and second expandable members are normally biased apart, but are restrained and held together by the tubular member. The Y-shaped stent is then delivered to a target area. The tubular member is withdrawn proximally until the first expandable member and the second expandable member are released and spring apart. The Y-shaped stent is next implanted by inflating the first and second expandable members. The first and second expandable members are then deflated and the catheter is withdrawn.

In yet another aspect of the invention, a method is provided of stenting a bifurcated vessel having a bifurcation, a first vessel branch, and a second vessel branch. The method includes the step of providing a dual balloon Y-shaped catheter including a first expandable member and a second expandable member. A first guide wire lumen is provided for receiving a first guide wire. The first guide wire lumen extends through at least a portion of the catheter including the first expandable member. A second guide wire lumen is provided for receiving a second guide wire. The second guide wire lumen extends through at least a portion of the catheter including the second expandable member. A Y-shaped stent is mounted on the first and second expandable members. A tubular member is placed about the first and second expandable members such that the first and second expandable members are normally biased apart, but are restrained and held together by the tubular member. A second guide wire is positioned distally of the bifurcation in the first vessel branch. The second guide wire is then backloaded into the second guide wire lumen. Next, the catheter and tubular member are advanced over the second guide wire so that the catheter is advanced distally of the bifurcation in the first vessel branch. Alternatively, the catheter can be advanced proximally of the bifurcation in the first vessel branch. The tubular member is withdrawn proximally until the first expandable member and the second expandable member are released and spring apart. Next, the catheter is withdrawn proximally to a position proximal of the bifurcation. A first guide wire is provided and advanced out of the first guide wire lumen and into the second vessel branch distally of the bifurcation. The catheter is advanced distally over the first and second guide wires until the Y-shaped stent is positioned at the bifurcation. The Y-shaped stent is then implanted by inflating the first and second expandable members. The first and second expandable members are deflated and the catheter and guide wires are withdrawn.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 5A is an elevational view of a bifurcation in which a prior art stent is implanted in the side branch vessel.

FIG. 5B is an elevational view of a bifurcation in which a prior art stent is implanted in the side branch vessel, with the proximal end of the stent extending into the main vessel.

FIG. 6 is an elevational view, partially in section, depicting an embodiment in which a Y-shaped catheter assembly deploys a Y-shaped stent in a bifurcation.

FIG. 7 is an elevational view depicting the Y-shaped catheter assembly of FIG. 6 in which the stent is mounted on the expandable members of the catheter.

DETAILED DESCRIPTION OF THE PREFERRED EMBODIMENTS

Figure 1:
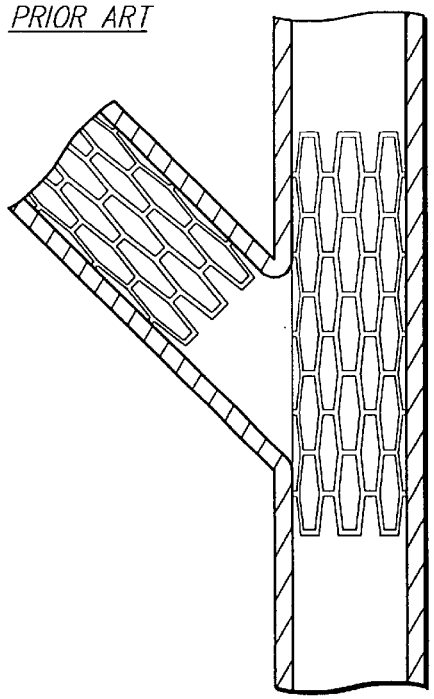
FIG. 1 is an elevational view of a bifurcation in which a prior art "T" stent is in a side branch ostium followed by the stenting of the main vessel across the branch ostium.

As shown in the exemplary drawings wherein like reference numerals indicate like or corresponding elements among the figures, the present invention includes a bifurcated stent delivery system for treating bifurcated vessels in, for example, the coronary arteries, veins, arteries, and other vessels in the body.

Prior art attempts at implanting intravascular stents in a bifurcation have proved less than satisfactory. For example, FIGS. 1–4 depict prior art devices which include multiple stents being implanted in both the main vessel and a side branch vessel. In FIG. 1, a prior art "T" stent is implanted such that a first stent is implanted in the side branch near the ostium of the bifurcation, and a second stent is implanted in the main vessel, across the side branch ostium. With this approach, portions of the side branch vessel are left uncovered, and blood flow to the side branch vessel must necessarily pass through the main vessel stent, causing possible obstructions or thrombosis.

Figure 2:
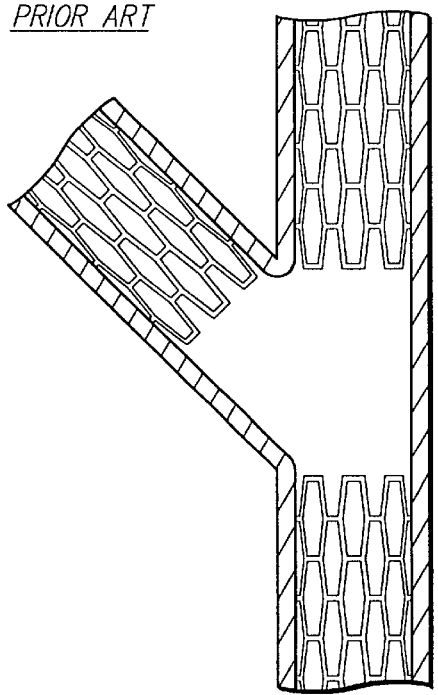
FIG. 2 is an elevational view of a bifurcation in which "touching" prior art stents are depicted in which one stent is implanted in the side branch, a second stent implanted in a distal portion of the main vessel next to the branch stent, with interrupted placement of a third stent implanted more proximally in the main vessel.
Figure 3:
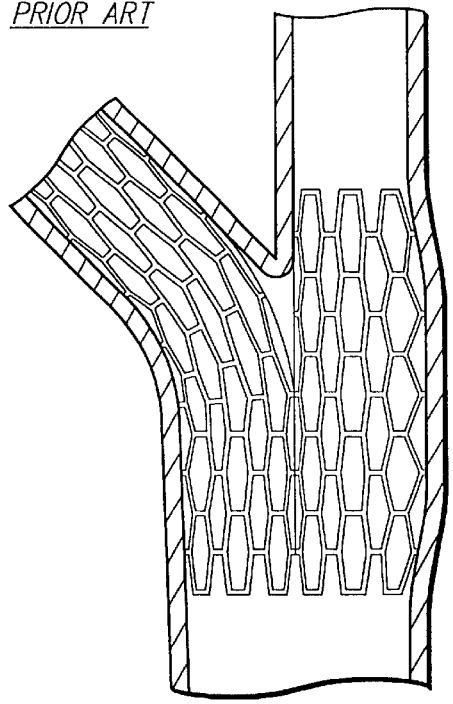
FIG. 3 is an elevational view of a bifurcation depicting "kissing" stents where a portion of one stent is implanted in both the side branch and the main vessel and adjacent to a second stent implanted in the main vessel creating a double-barreled lumen in the main vessel proximal to the bifurcation.
Figure 4:
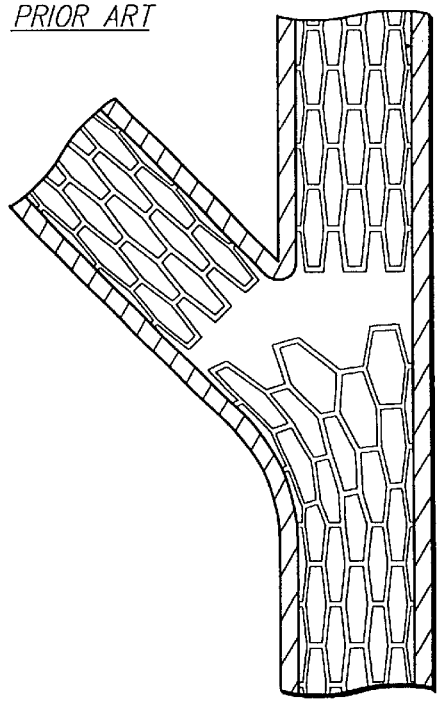
FIG. 4 is an elevational view of a prior art "trouser legs and seat" stenting approach depicting one stent implanted in the side branch vessel, a second stent implanted in a proximal portion of the main vessel, and a close deployment of a third stent distal to the bifurcation leaving a small gap between the three stents of an uncovered lumenal area.
Figure 8:
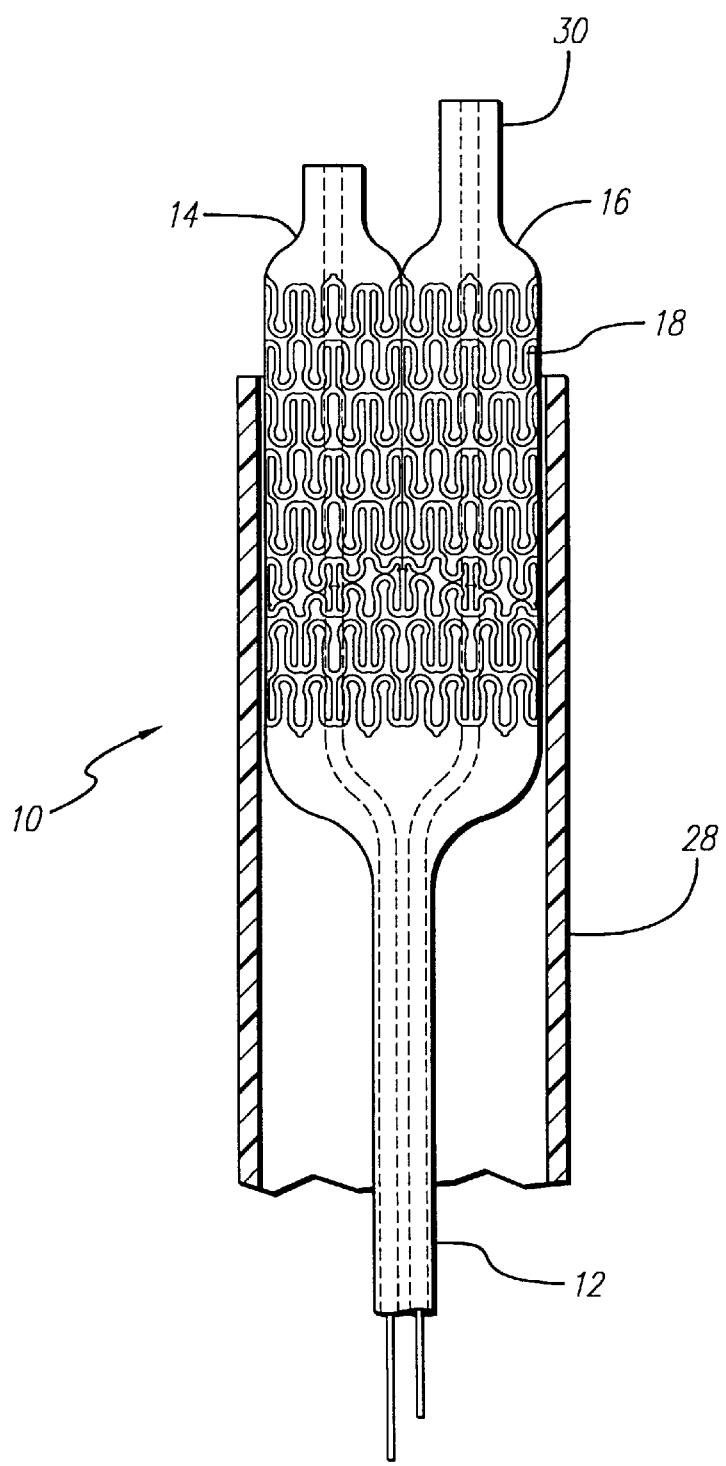
FIG. 8 is a perspective view of the assembly of FIG. 7 shown partially inserted into the sheath.
Figure 9:
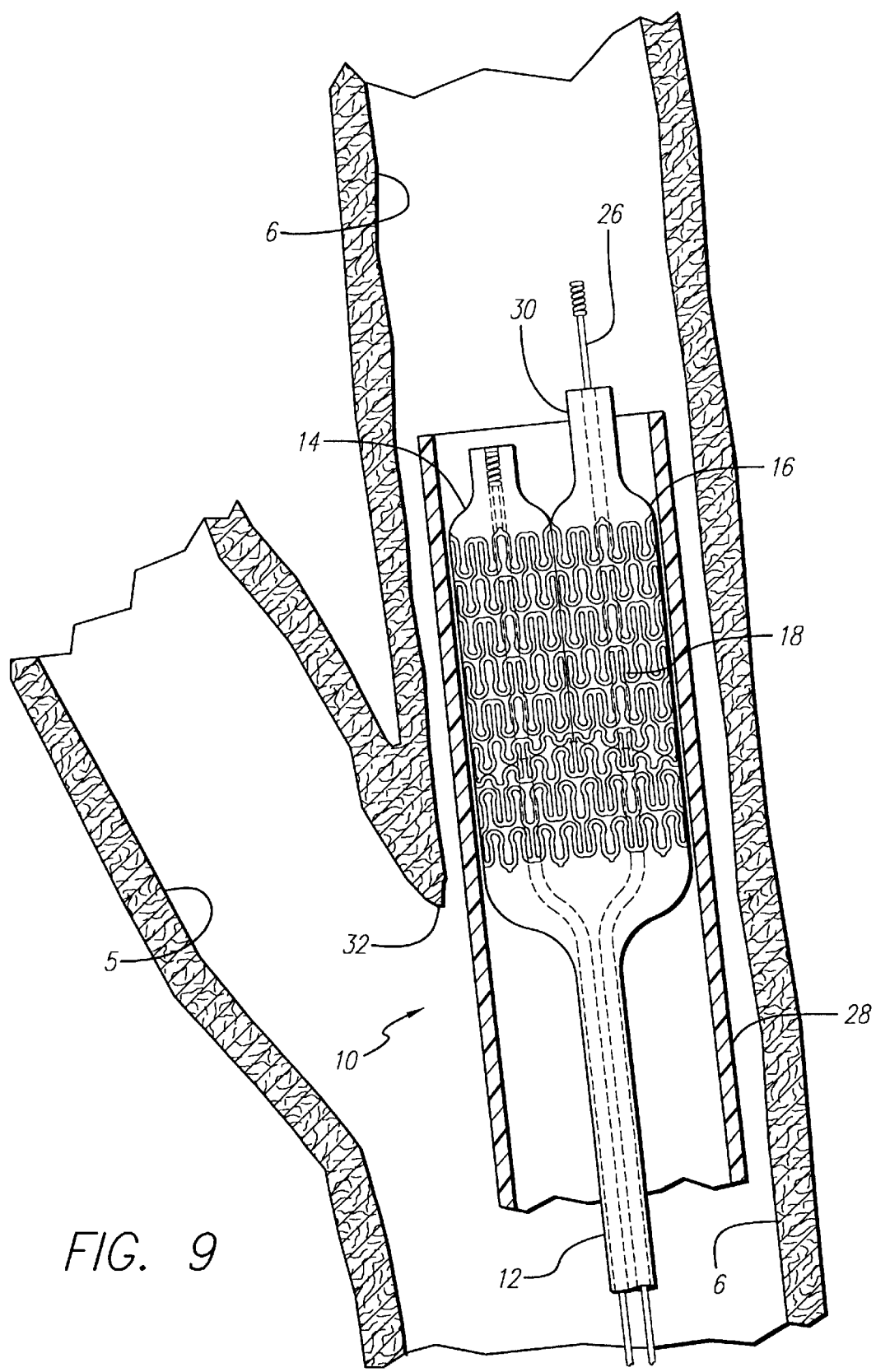
FIG. 9 is an elevational view, partially in section, of a bifurcation in which the catheter of FIG. 7 is delivering the stent in the bifurcated area with the catheter inserted into the sheath.
Figure 10:
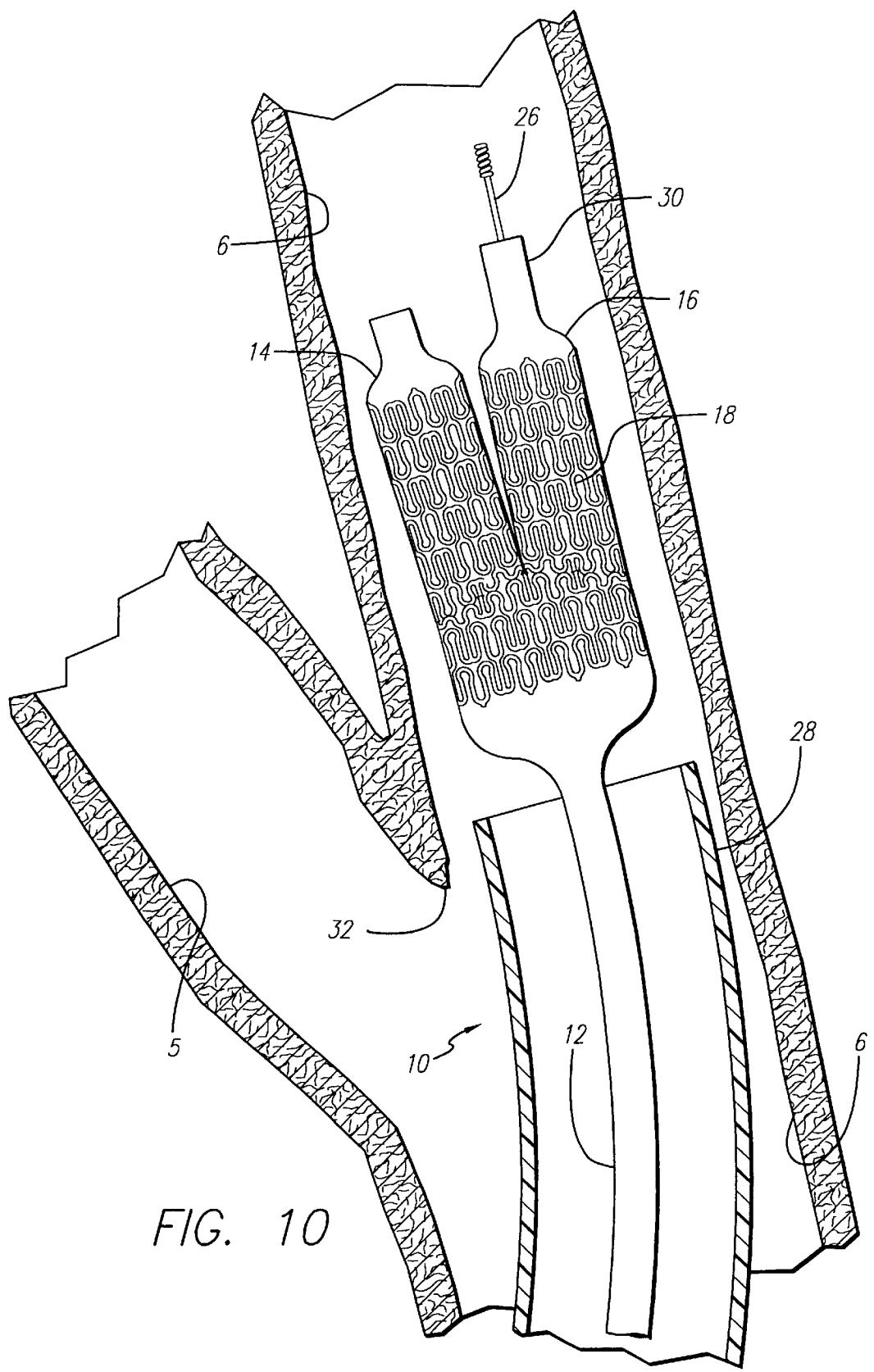
FIG. 10 is an elevational view, partially in section, of a bifurcation in which the catheter of FIG. 7 is delivering the stent in the bifurcated area with the sheath being withdrawn proximally.
Figure 11:
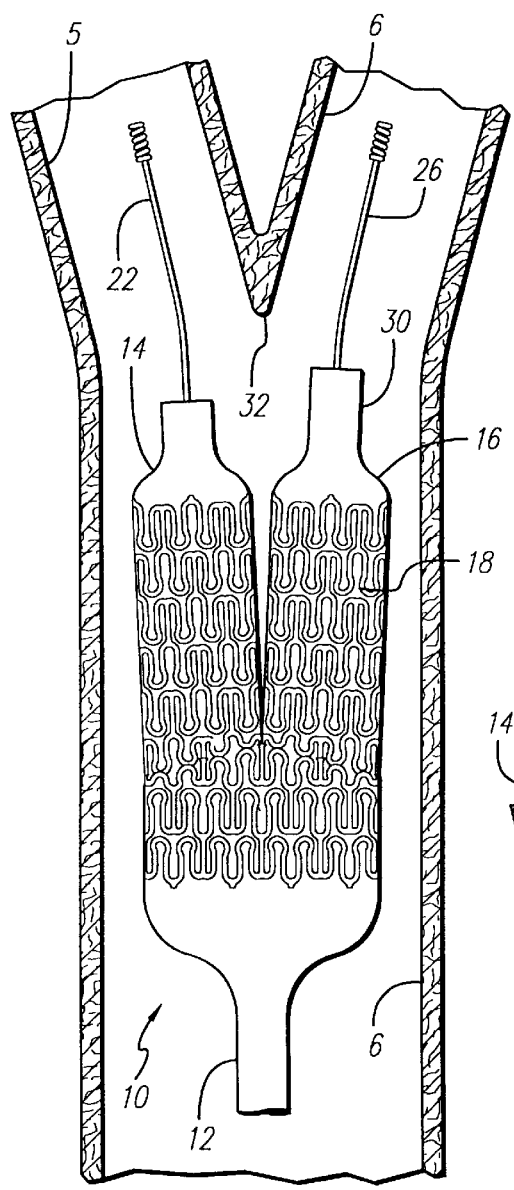
FIG. 11 is an elevational view, partially in section, of a bifurcation in which the catheter of FIG. 7 has been withdrawn proximally of the bifurcation and a guide wire is being extended into the second vessel branch.
Figure 12:
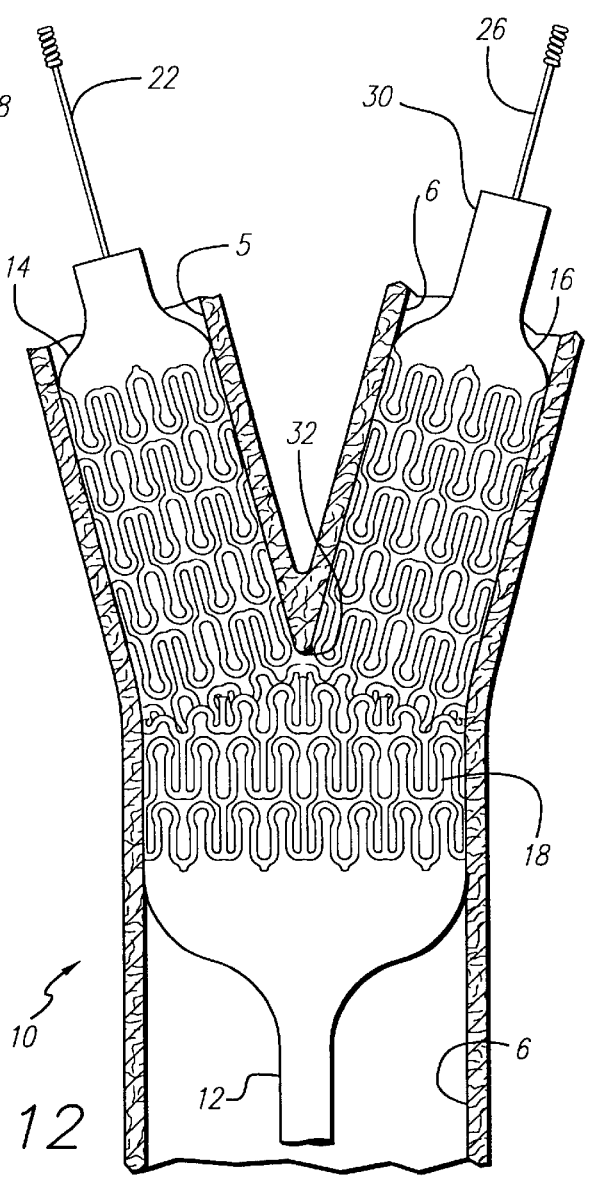
FIG. 12 is an elevational view, partially in section, of a bifurcation in which the catheter of FIG. 7 is implanted at the bifurcation.

Referring to FIG. 2, three prior art stents are required to stent the bifurcation. In FIG. 3, the prior art method includes implanting two stents side by side, such that one stent extends into the side branch vessel and the main vessel, and the second stent is implanted in the main vessel. This results in a double-barreled lumen which can present problems such as thrombosis, and turbulence in blood flow. Referring to the FIG. 4 prior art device, a first stent is implanted in the side branch vessel, a second stent is implanted in a proximal portion of the main vessel, and a third stent is implanted distal to the bifurcation, thereby leaving a small gap between the stents and an uncovered lumenal area.

Referring to FIGS. 5A and 5B, a prior art stent is configured for deployment in side branch vessel 5. In treating side branch vessel 5, if a prior art stent is used, a condition as depicted will occur. That is, a stent deployed in side branch vessel 5 will leave a portion of the side branch vessel exposed, or as depicted in 5B, a portion of the stent will extend into main vessel 6.

Turning to FIGS. 6–12, in one embodiment of the present invention, stent delivery assembly 10 is provided for treating bifurcated vessels. In this embodiment, a Y-shaped stent is implanted to cover the bifurcation. Catheter 12 can be configured as a dual balloon Y-shaped catheter having a proximal end and a distal end. The catheter includes first expandable member 14 and second expandable member 16 that are configured to reside side-by-side (Y-shaped) for low profile delivery and to spring apart for implanting Y-shaped stent 18. Each of the expandable members has a proximal end and a distal end. The stent is removably mounted on the first and second expandable members.

A first guide wire lumen 20 is provided for receiving first guide wire 22. The first guide wire lumen extends through at least a portion of catheter 12 including first expandable member 14. A second guide wire lumen 24 is provided for receiving second guide wire 26. The second guide wire lumen extends through at least a portion of the catheter including second expandable member 16. The expandable members can be inflatable non-distensible balloons. The guide wires 22, 26 preferably are stiff wires each having a diameter of 0.014 inch, but can have different diameters and degrees of stiffness as required for a particular application. A particularly suitable guide wire can include those manufactured and sold under the tradenames Sport® and Ironman®, manufactured by Advanced Cardiovascular Systems, Incorporated, Santa Clara, Calif.

A tubular member, such as sheath 28, is provided, wherein the first expandable member and the second expandable member are normally biased apart, but are restrained and held together by the sheath to provide a low profile during delivery of Y-shaped stent 18. The sheath can be formed from a polymer such as polyethylene, polyurethane, and nylons, although other similar polymeric material may also be suitable, such as polyetheretherketone (PEEK), polytetrafluoroethylene (PTFE), polyethylene terephthalate (PET), and the like. Other suitable materials can be used as are known to those skilled in the art.

The catheter 12 further includes an inflation lumen (not shown) for inflating first and second expandable members 14, 16 simultaneously. The expandable members can be inflated by delivering a suitable inflation media, such as saline, to the expandable members via the inflation lumen. In one embodiment, the second expandable member is longer than the first expandable member so that distal portion 30 of the second expandable member protrudes from sheath 28 during delivery to facilitate tracking.

In one method of stenting a bifurcated vessel, as shown in FIGS. 9–12, Y-shaped stent 18 is mounted on first and second expandable members 14, 16. The second guide wire 26 is positioned distal of the bifurcation in first vessel branch 6. The second guide wire is then back loaded into second guide wire lumen 24. The catheter 12 and sheath 28 are advanced over the second guide wire so that the catheter is advanced distally of the bifurcation in the first vessel branch. During the advancement of the catheter, the first and second expandable members are restrained and held together by sheath. Consequently, the sheath helps to provide a low profile during delivery of the stent.

In keeping with the invention, sheath 28 is withdrawn proximally until first expandable member 14 and second expandable member 16 are released and spring apart. The catheter 12 is then withdrawn proximally to a position proximal of the bifurcation. In one embodiment, first guide wire 22 has been contained as an integrated guide wire within first guide wire lumen 20 up to this point. Alternatively, the first guide wire may be inserted into the proximal end of the first guide wire lumen at this time. The first guide wire is then advanced out of the first guide wire lumen and into second vessel branch 5 distally of the bifurcation.

If, after withdrawal of the sheath to release the expandable members, the device is seen to be oriented such that first expandable member 14 is further away from vessel 5 than is second expandable member 16, it may be desirable to withdraw second guide wire 26 and readvance it into vessel 5 with first guide wire 22 then advanced into vessel 6. This reassignment of wires permits avoidance of rotation of more than 90 degrees. In situations in which there is concern about recrossing of the lumen of the side branch vessel with either wire, this wire reassignment is performed before catheter 12 is withdrawn proximal to the bifurcation.

The Y-shaped stent 18 is implanted by advancing distally over first and second guide wires 22,26 until the stent is positioned at the bifurcation in apposition with carina 32. Due to the appropriate wire selection, rotation of no more than 90 degrees will be required. The stent is implanted by inflating first and second expandable members 14, 16, which are designed to inflate simultaneously. Then the first and second expandable members are deflated and the catheter and guide wires can be withdrawn from the patient's vasculature. The novel arrangement of sheath 28 and guide wires 22, 26 and their respective lumens permit single unit transport of a Y-shaped stent to the distal target site without wire wrapping problems and it allows for minimal requirements of rotation of the device (less than 90 degrees) for optimal deployment (allowing minimal twist deformity).

In a related method, Y-shaped stent 18 is mounted on first and second expandable members 14, 16. The second guide wire 26 is positioned distal of the bifurcation in first vessel branch 6. The second guide wire is then back loaded into second guide wire lumen 24. The catheter 12 and sheath 28 are advanced over the second guide wire so that the catheter is advanced proximally of the bifurcation in the first vessel branch. During the advancement of the catheter, the first and second expandable members are restrained and held together by the sheath. Consequently, the sheath helps to provide a low profile during delivery of the stent.

In keeping with the invention, sheath 28 is withdrawn proximally until first expandable member 14 and second expandable member 16 are released and spring apart. In one embodiment, first guide wire 22 has been contained as an integrated guide wire within first guide wire lumen 20 up to this point. Alternatively, the first guide wire may be inserted into the proximal end of the first guide wire lumen at this time. The first guide wire is then advanced out of the first guide wire lumen and into second vessel branch 5 distally of the bifurcation.

Next, catheter is advanced distally over first and second guide wires 22, 26 until Y-shaped stent 18 is positioned at the bifurcation in apposition with carina 32. Due to the appropriate wire selection, rotation of no more than 90 degrees will be required. The stent is implanted by inflating first and second expandable members 14, 16, which are designed to inflate simultaneously. Then the first and second expandable members are deflated and the catheter and guide wires can be withdrawn from the patient's vasculature. The novel arrangement of sheath 28 and guide wires 22, 26 and their respective lumens permit single unit transport of a Y-shaped stent to the distal target site without wire wrapping problems and it allows for minimal requirements of rotation of the device (less than 90 degrees) for optimal deployment (allowing minimal twist deformity).

Figure 13:
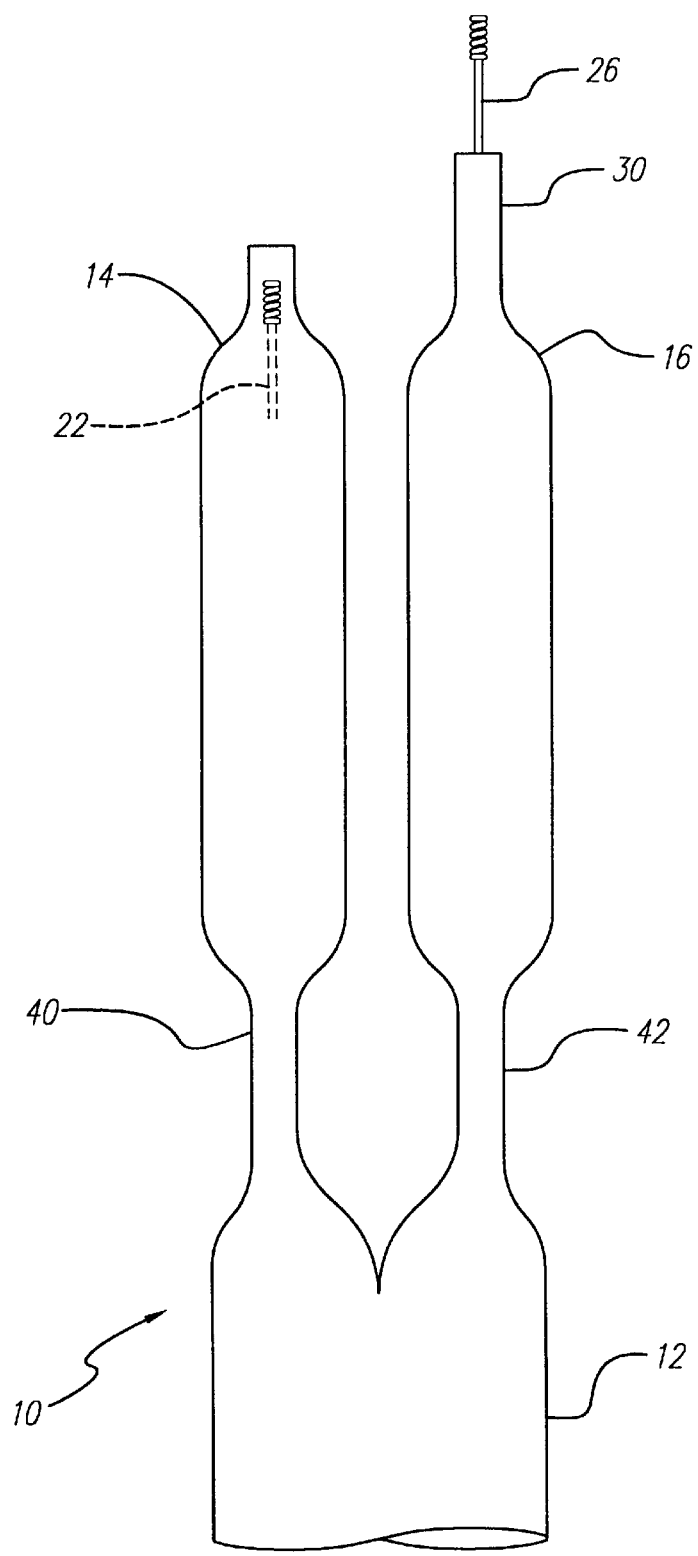
FIG. 13 is another embodiment of the dual balloon Y-shaped catheter.
Figure 14:
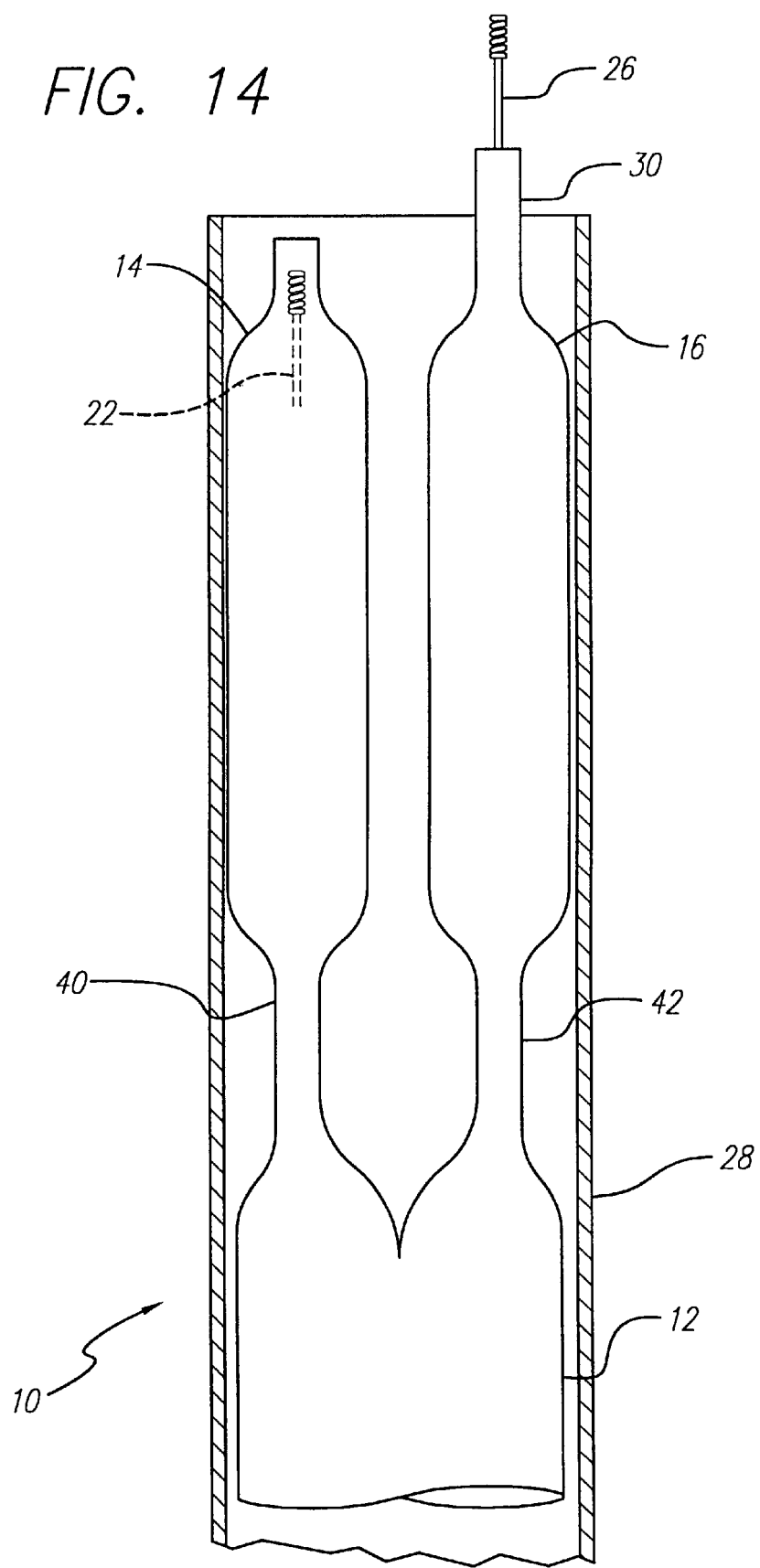
FIG. 14 is an elevational view, partially in section, of the dual balloon Y-shaped catheter of FIG. 13 restrained by the sheath.

Notably, it is contemplated that the methods of the present invention can be accomplished with any suitable catheter 12. Referring to FIGS. 13 and 14, another embodiment of the dual balloon Y-shaped catheter is depicted. The catheter has first stem 40 and second stem 42. The first stem 40 is connected to first expandable member 14. The second stem 42 is connected to second expandable member 16 having distal portion 30 for tracking. In this embodiment, the second expandable member is approximately twice as long as the first expandable member; however, it is contemplated that the expandable members can be of varying lengths. The expandable members can be simultaneously inflated via an inflation lumen (not shown). The first guide wire 22 is positioned within the first expandable member and the second guide wire is positioned within the second expandable member. The first and second expandable members are normally biased apart, but are restrained and held together by sheath 28 to provide a low profile during delivery of Y-shaped stent 18.

While the invention herein has been illustrated and described in terms of a catheter assembly and method of use, it will be apparent to those skilled in the art that the invention can be used in other instances. Other modifications and improvements may be made without departing from the scope of the invention.

What is claimed is:

1. A stent delivery assembly for treating bifurcated vessels, comprising:
   a dual balloon Y-shaped catheter having a proximal end and a distal end, the catheter including a first expandable member having a proximal end and a distal end, the catheter further including a second expandable member having a proximal end and a distal end;
   a first guide wire lumen for receiving a first guide wire, the first guide wire lumen extending through at least a portion of the catheter including the first expandable member;
   a second guide wire lumen for receiving a second guide wire, the second guide wire lumen extending through at least a portion of the catheter including the second expandable member; and a tubular member;

wherein the first expandable member and the second expandable member are normally biased apart, but are restrained and releasably held together by the tubular member to provide a low profile during delivery of a Y-shaped stent.

2. The assembly of claim 1, wherein the tubular member is a sheath.

3. The assembly of claim 1, wherein the Y-shaped stent is removably mounted on the first and second expandable members.

4. The assembly of claim 1, further including an inflation lumen for inflating the first and second expandable members.

5. The assembly of claim 4, wherein the first and second expandable members inflate simultaneously.

6. The assembly of claim 1, wherein the second expandable member is longer than the first expandable member.

7. The assembly of claim 6, wherein when the first expandable member and the second expandable member are restrained and held together by the tubular member, a distal portion of the second expandable member protrudes from a distal end of the tubular member.

* * * * *

UNITED STATES PATENT AND TRADEMARK OFFICE
CERTIFICATE OF CORRECTION

PATENT NO.    : 6,254,593 B1
DATED         : July 3, 2001
INVENTOR(S)   : W. Stan Wilson It is certified that error appears in the above-identified patent and that said Letters Patent is hereby corrected as shown below:

Title page,
Under "FOREIGN PATENT DOCUMENTS", change "WO 97/", to read
-- WO 97/16217 --.

Signed and Sealed this

Twenty-ninth Day of January, 2002

Attest:

JAMES E. ROGAN
Attesting Officer
Director of the United States Patent and Trademark Office